United States Patent [19]
Hultman

[11] Patent Number: 4,477,433
[45] Date of Patent: Oct. 16, 1984

[54] METHOD OF PROTECTING BUSHES, TREES AND LIKE PLANTS AGAINST ATTACK BY PATHOGENIC FUNGI; A FUNGICIDE FOR CARRYING OUT THE METHOD; AND A METHOD OF PRODUCING THE FUNGICIDE

[75] Inventor: Rolf Ö. Hultman, Bro, Sweden

[73] Assignee: Miliokonsult Rolf Hultman AB, Bro, Sweden

[21] Appl. No.: 348,134

[22] Filed: Feb. 11, 1982

[30] Foreign Application Priority Data

Feb. 19, 1981 [SE] Sweden ................................ 8101113

[51] Int. Cl.$^3$ ..................... A01N 63/00; A61K 37/00; C12N 1/14
[52] U.S. Cl. ........................................... 424/93; 71/3; 435/254
[58] Field of Search .................. 424/93; 435/254, 911, 435/929, 939, 945; 71/3

[56] References Cited

FOREIGN PATENT DOCUMENTS 161312 12/1981 Japan ..................................... 424/93
1090403 11/1967 United Kingdom .................. 424/93
302914 1/1979 U.S.S.R. ................................ 424/93

Primary Examiner—Blondel Hazel
Attorney, Agent, or Firm—Fred Philpitt

[57] ABSTRACT

The invention relates to a method and fungicide for protecting flowering plants, bushes, trees and like plants against attack from pathogenic fungi, by treating the plants with fungi which are antagonistic toward the pathogenic fungus, wherein the earth in which the flowering plants, bush, tree or like plant is intended to grow, or grows, is treated with a product obtained by cultivating the antagonistic fungus on a cultivating substrate comprising compost material obtained by biologically decomposing organic compostible material and treated for exterminating microorganisms which inhibit cultivation of the antagonistic fungus. The invention also relates to a method for producing a fungicide which will protect flowering plants, bushes, trees and like plants from attack in accordance with the above.

8 Claims, No Drawings

METHOD OF PROTECTING BUSHES, TREES AND LIKE PLANTS AGAINST ATTACK BY PATHOGENIC FUNGI; A FUNGICIDE FOR CARRYING OUT THE METHOD; AND A METHOD OF PRODUCING THE FUNGICIDE

The present invention relates to a method of protecting flowering plants, bushes, trees and like plants against attack from pathogenic fungi, by treating the plants with fungi which are antagonistic toward the pathogenic fungi. The invention also relates to a fungicide for carrying out the method, and to a method of producing the fungicide.

It is well known that the soil used for cultivating plants contains many different types of fungi. Many of these fungi are pathogenic and can bring disease to the plants. Diseased plants result in poor plant yield and/or in an impaired quality of the plants harvested.

It is also known that the pathogenic fungi present in the soil can be controlled biologically, by adding antagonistic substances thereto. According to one suggested method, these antagonistic substances are added directly to the ground represented by the cultivating soil, in the form, for example, of suspensions of the fungi in an aqueous medium. According to another method, it is proposed that the antagonistic fungus is grafted on the seed from which the plant or plants are to be grown. None of the proposed solutions, however, have been found particularly suitable in practice. In conjunction with tests on which the present invention is based, it has been found that certain composts obtained when composting compostible material, such as domestic waste, sewage sludge, which in conjunction with the composting process has been treated at a relatively high temperature, for example a temperature of 70°-80° C., for a relatively long period of time, for example for 50 hours (2 calendar days) or longer, constitute an extremely favourable substrate for cultivating fungi antagonistic to pathogenic fungi, which, as before mentioned, cause plants to become diseased. Such composts, in which the antagonistic fungi in question is cultivated to a given minimum content, form a suitable fungicide for soil which is to be used, or is used, for cultivating plants liable to attack from pathogenic fungi. By introducing suitable quantities of the fungicide into the soil, it is possible to completely eliminate, or substantially reduce the risk of attack from a number of pathogenic fungi. The main reason why the compost material is well suited as a cultivating substrate for antagonistic fungi is that during the manufacture of the compost it is subjected to treatment at high temperature, and thereby contains far less fungi capable of inhibiting the cultivation of the antagonistic fungi in question than would otherwise be the case. The compost contains mainly only thermofilic fungi, while other fungi are eradicated. A number of spore-forming bacteria remain in the compost, but they have no inhibiting affect on the subsequent cultivating process. The compost also contains a certain amount of cellulose, which is an advantage since the antagonistic fungi in question degrade cellulose. Because part of the process by which the compost is formed takes place at said relatively high temperature and over a relatively long period of time, all microorganisms antagonistic toward the antagonistic fungi in question have been eradicated. In addition to supplying the antagonistic fungi in question, the compost used as the cultivating medium also acts as a carrier. The fungicide can be readily spread by mechanical means over ground in which pathogenic fungi is to be eradicated.

On the basis of the aforegoing, the present invention is characterized by treating the soil in which the bush, tree or like plant is intended to grow, with a product obtained by cultivating antagonistic fungi on a cultivating substrate comprising compost material obtained by biologically decomposing organic compostible material, said cultivating substrate being treated to kill microorganisms which inhibit the cultivation of antagonistic fungi.

It has been found that the desirable properties of the cultivating substrate can suitably be obtained by treating the compost material at a temperature of at least about 70° C. over a period of time of at least about 50 hours (about 2 calendar days) prior to the cultivating process. When treating compostible material in this manner, microorganisms present in said material will be killed, with the exception of thermophilic microorganisms, which are able to withstand temperatures of at least about 70° C. over a period of about 50 hours or longer.

To facilitate application of the fungicide, the compost material is suitably formed into granules, for example so-called pellets, having a particle size of, for example, 3-4 mm, suitable for use with agricultural machinery.

The compost is suitably obtained from different compostible mixtures, by treating said mixtures in a reactor vessel, in which the material to be composted is charged to the top of reactor vessel and the composted material removed from the bottom thereof, and in which the material moves downwardly through the reactor vessel in contact with a stream of oxygen-containing medium, preferably air, which is introduced to the bottom of said vessel. In this way, different temperature zones are created in the reactor vessel, in which zones different types of microorganisms exert a maximum decomposing effect on the compostible material. At the bottom of the reactor vessel, the material being composted is caused to pass into a high-temperature zone, in which the temperature can lie between about 70° and 80° C. This high temperature causes all disease-generating microorganisms to be killed, provided that the material remains in said zone for a sufficiently long period of time, which is normally more than about 2 calendar days, while the so-called thermophilic fungi continue to exercise a decomposing effect on the material, to form a structure-improving mycelium (vide, for example, U.S. patent specification No. 4,249,929). One prerequisite for a waste material to be combustible is that it comprises a nutruent for microorganisms, particularly fungi. In this respect, one condition is that the starting material to be composted by biological decomposition has a carbon/nitrogen balance lying between 25:1 and 40:1. Waste material containing carbon and nitrogen in a ratio lying outside these limits must be provided with additive substances, so as to obtain a carbon/nitrogen ratio which meets the above condition. When the material to be composted contains too little carbon for the process of decomposition to take place satisfactorily with the aid of microorganisms, the material can be admixed with a suitable carbon carrier, for example sawdust or wood shavings. If the material requires more nitrogen, a suitable nitrogen carrier, such as urea, ammonium salts, can be incorporated in the material.

Thus, when composting compostible material, such as domestic waste and sewage sludge, in reactor vessels in accordance with the above, there is obtained a hygienic compost, which when discharged from the reactor vessel normally has an elevated temperature of about 25°-35° C. and contains nutrients for antagonistic fungi. A prime nutrient is the cellulose present in the compost. At temperatures within the aforegiven range, the fungi in question will grow very rapidly and obtain an ecological advantage over other fungi and other microorganisms through their ability to effectively break down the cellulose.

There is also obtained by means of the invention an agent for controlling plant disease, which enables the fungi antagonistic to pathogenic fungi to be brought into the vicinity of the seed, the roots of the plant and the developing shoots thereof. In addition to forming a suitable carrier for applying and spreading the antagonistic fungi on the ground, the compost material, which has served as a substrate for cultivating said antagonistic fungi, also constitutes a suitable fungi storage for the period over which it is intended to act against pathogens in the ground.

The fungi added to the compost used as a substrate for their cultivation can originate from a previous cultivation of the same fungi, wherein a minor part of the cultivated material is recycled. When the method is carried out for the first time, the substrate is suitably innoculated with fungi cultivated on a sterile liquid medium.

As beforementioned the invention also relates to a fungicide for carrying out the method. One such fungicide capable of protecting plant life against attack from pathogenic fungi comprises a mixture containing living mycel of fungi which are antagonistic towards the pathogenic fungi, and spores of antagonistic fungi. The fungicide is characterized in that the mixture also contains compost material obtained by biologically decomposing organic combustible material, which combustible material has been treated to kill microorganisms of the kind which disturb or inhibit the cultivation of antagonistic fungi. This result is preferably achieved by treating the compost material at a temperature of at least about 70° C. over a period of about 50 hours (2 calendar days) or longer.

The fungicide according to the invention can be produced by a method characterized in that fungi which are antagonistic toward pathogenic fungi, which bring disease to plant life, such as bushes and trees, are cultivated on a substrate comprising compost material which has been treated to kill those microorganisms which disturb or inhibit the cultivation of antagonistic fungi, preferably at a temperature of at least about 70° C. for a period of about 2 calendar days or longer. This treatment of the compost material is preferably effected in conjunction with the composting process. Treatment of the compost material in this respect, however, may also be undertaken in a treatment stage, which although connected to the composting process is separate therefrom.

Examples of pathogenic fungi which attack plant life include, for example, corn and wheat rust and witchweed, root rot of peas and beets, snow mould on grass, potato blight and blackspot on roses. These pathogens can be controlled with different strains of the genera Trichoderma and Gliocladium. One extremely important advantage with such strains is that they split cellulose, and thus grow and multiply on cellulosic substrates. Since compost nearly always contains cellulose, it is particularly suitable as a cultivating medium for the antagonistic fungus. Since earth used to cultivate plants contains residues of cellulosic material, such as roots, branches, stubs, straw etc., multiplication of the fungi is able to continue even when the fungicide has been applied.

A number of the genera Trichoderma which can be used for biologically controlling pathogens in soil used for plant cultivation are given in the Table below.

| Trichoderma-species | Pathogen | Protected Host Plant |
|---|---|---|
| T. koningi | Gaeumannomyces graminis | Spring Wheat |
| T. harzianum | Sclerotium rolfsii | Blue Lupins peanuts, tomatoes |
| T. harzianum | Pythium aphanidermatum | Tobacco |
| T. harzianum | R. solani S. rolfsii | Beans, peanuts, eggplants |
| T. harzianum | R. solani | Tomatoes |
| T. sp | Botrytis cinera | Strawberries |
| T. sp | Verticillium fungicola | Mushrooms |
| T. viride | Fusarium roseum Avenaceum | Lentils |
| T. viride | Stereum purpuream | Plum Trees |

Other plant pathogens are *Gaeumannomyces graminis* and *Fusarium Nivale*.

After rust (Puccinia), *G. graminis* is the most harmful to wheat. An attack by *G. graminis* is manifested by patches of weakly stemmed plants which have ripened prematurely and are of stunted growth. The diseased plants can be easily pulled out of the ground, since the disease results in a poorly developed root system. When the prematurely ripened plant dies, spores are formed on the stub and straw, and in this way the fungus is able to survive the winter.

Consequently, the root killer has a practical significance when growing wheat and maize, and in normal years is calculated to destroy about 10–15% of the shoots. Such attack is mainly prevalent in the cereal-growing districts of southern and central Sweden. The loss of harvest in these districts has been calculated to 80 million Swedish kronor in maize and 75 million kronor in wheat, calculated on the 1975 prices.

*Fusarium nivale* (snow mould) causes damage to wintering leaves. Attack by this fungus occurs primarily during winters when a layer of snow lies on unfrozen ground. *F. nivale* is able to multiply in the low temperature and low oxygen environment and the high carbon dioxide environment existing beneath the snow. Fusarium-species can also inhibit germination of the seed, when the seed germs are infected by spores carried on the speed. Such infection results in small and crooked seed germs, and the germs are often so weakened as to prevent them from reaching to the surface of the ground. Fusarium attack is greatly dependent on the prevailing climatic conditions. Consequently, the frequency at which such attack takes place varies greatly. Annual wintering losses caused by snow mould have been estimated to be 34 million Swedish kronor for autumn wheat and 9 million Swedish kronor for rye. When taken together, the losses caused by other Fusarioses are estimated to be of the same order of magnitude.

EXAMPLE

The following known antagonistic fungi were used in the tests:

A. *Trichoderma koningi*

B. Trichoderma sp.

The fungi were stored in inclined agar tubes with malt extract.

The fungi were cultivated on discs of a cellulosic substance (comprising cellulosic waste from the paper-making industry containing short-fibre cellulose and kaolin). The discs, punched from a sheet of said substance, had a diameter of 2 cm and were placed on 1% agar containing nitrogen and salts in accordance with the following (given in g/1000 ml distilled water). The pH of all solutions was set to about 7.0 with the aid of sodium hydroxide and dilute hydrochloric acid.

| (1) $(NH_4)_2HPO_4$ | 2.5 |
|---|---|
| KCl | 0.5 |
| $MgSO_4.7H_2O$ | 0.5 |
| $FeSO_4.7H_2O$ | 0.01 |
| (2) $(NH_4)_2HPO_4$ | 2.5 |
| KCl | 0.5 |
| $MgSO_47H_2O$ | 0.5 |
| (3) $(NH_4)_2HPO_4$ | 2.5 |
| KCl | 0.5 |
| (4) $(NH_4)_2HPO_4$ | 2.5 |

The Trichoderma-strains A and B were then innoculated centrally on the plates. Over days 4–7 the growth of the strains was measured by mycel propagation and by estimating the sporulation of the fungus. All solutions (1)–(4) above resulted in very good growth.

For further cultivation of the resultant fungus material there was used a compost obtained by decomposing compost material deriving from a mixture of domestic waste and sewage sludge from a sewage purification plant. Decomposition of the compost material was effected in a reactor vessel during migration of the material downwardly through the vessel from the top thereof, while simultaneously bringing air into contact with the downwardly moving material (such a plant is at present being used by the municipalities of Landskrona, Sweden). As the compost material migrates downwardly through the reactor vessel, the material was retained in a zone which had a temperature of 70°–85° C., with the result that all microorganisms were killed, with the exception of thermophilic microorganisms and spore-forming bacteria.

The resultant compost was finely divided in a mixer and admixed with distilled water. In this way there was obtained a material from which discs having a diameter of 2 cm and a thickness of 4 mm could be punched. The discs were placed on 1% agar with ammonium diphosphate (2.5 g/l) phosphate-buffered (0.02$MPO_4^{-3}$) to a pH of 6.0. An isolate of each of the trichoderma-strains obtained above was then applied to respective discs. It was found with both strains that the compost provided an extremely good substrate for further growth of the fungi. It was not necessary to add nitrogen to the compost.

Compost having a temperature of about 35° C. and taken directly after being discharged from the reactor vessel was provided with the fungus-containing liquids obtained in the test. Subsequent to slowly stirring the compost mixture for some period of time, there was obtained a preparation which was well suited for controlling pathogens.

Antagonistic fungi cultivated on substrates of compost free from living microorganisms, other than thermophilic microorganisms, have been tested against the following pathogens with good results:

I *Fusarium solani*
IV *Verticillium dahliae*
V *Gaeumannomyces graminis*
VI *Fusarium nivale.*

I claim:

1. A method of protecting plants, bushes and trees against attack from pathogenic fungi by treating the soil in which the plant, bush or tree is intended to grow with fungi antagonistic towards the pathogenic fungus, wherein the improvement comprises cultivating the antagonistic fungus on a cultivating substrate comprising compost material obtained by biologically decomposing organic compostible material and treating compostible material at a temperature of at least about 70° C. over a period of at least about 2 calendar days to kill microorganisms which inhibit the cultivation of the antagonistic fungus.

2. A method according to claim 1 wherein the soil is treated with granules or "pellets" of compost material containing the antagonistic fungus.

3. A method according to claim 1 or 2 wherein the soil is simultaneously treated with a fertilizing agent.

4. A fungicide able to protect plants, bushes and trees against attack from pathogenic fungi, comprising a mixture of living fungi antagonistic toward the pathogenic fungus, and mycelia of said antagonistic fungus, wherein the improvement comprises further including a compost produced by biologically decomposing compostible material and treating it at a temperature of at least 70° C. for a period of at least about 2 calendar days to thereby exterminate microorganisms of the kind inhibitive to the cultivation of the antagonistic fungus, whereby said compost provides a cultivating substrate for the antagonistic fungi.

5. A fungicide according to claim 4 characterized in that the compost is in granular or particle form.

6. A fungicide according to claim 4 or 5 characterized in that the fungicide contains one or more fertilizers of the NPK-type.

7. A method of producing a fungicide capable of protecting plants, bushes and trees against attack from pathogenic fungi by adding therebo fungi which are antagonistic toward the pathogenic fungi, wherein the improvement comprises cultivating the antagonistic fungi, on a substrate comprising a compost material obtained by biological decomposition and treatment of compostible material at a temperature of at least about 70° C. over a period of at least 2 calendar days.

8. A method according to claim 7 characterized in that the compost material is treated at a temperature of 70°–85° C.

* * * * *